United States Patent
Lee et al.

(10) Patent No.: US 12,037,580 B2
(45) Date of Patent: Jul. 16, 2024

(54) DNA-PEPTIDE COMPOSITE COMPRISING HIGH-DENSITY FUNCTIONAL GROUP, DNA-PEPTIDE-NANOMATERIAL COMPOSITE AND PREPARATION METHOD THEREFOR, AND DNA-METAL NANOWIRE AND MANUFACTURING METHOD THEREFOR

(71) Applicants: Research & Business Foundation Sungkyunkwan University, Suwon-si (KR); Sogang University Research Foundation, Seoul (KR)

(72) Inventors: Jung Heon Lee, Seoul (KR); Kyu Bong Jo, Seoul (KR); Kyung Il Kim, Suwon-si (KR); Seong Hyun Lee, Gunpo-si (KR); Su Ji Kim, Suwon-si (KR); Xuelin Jin, Seoul (KR)

(73) Assignees: Research & Business Foundation Sungkyunkwan University, Suwon-si (KR); Sogang University Research Foundation, Seoul (KR)

( * ) Notice: Subject to any disclaimer, the term of this patent is extended or adjusted under 35 U.S.C. 154(b) by 828 days.

(21) Appl. No.: 16/346,187

(22) PCT Filed: Oct. 31, 2017

(86) PCT No.: PCT/KR2017/012117
§ 371 (c)(1),
(2) Date: Apr. 30, 2019

(87) PCT Pub. No.: WO2018/080273
PCT Pub. Date: May 3, 2018

(65) Prior Publication Data
US 2020/0056172 A1    Feb. 20, 2020

(30) Foreign Application Priority Data
Oct. 31, 2016    (KR) .................. 10-2016-0142832

(51) Int. Cl.
| | | |
|---|---|---|
| C12N 15/11 | (2006.01) |
| C07H 21/04 | (2006.01) |
| C07K 2/00 | (2006.01) |
| C12Q 1/6834 | (2018.01) |
| B82Y 5/00 | (2011.01) |
| B82Y 10/00 | (2011.01) |
| B82Y 30/00 | (2011.01) |

(52) U.S. Cl.
CPC ............ *C12N 15/11* (2013.01); *C07H 21/04* (2013.01); *C07K 2/00* (2013.01); *C12Q 1/6834* (2013.01); *B82Y 5/00* (2013.01); *B82Y 10/00* (2013.01); *B82Y 30/00* (2013.01); *C12N 2310/3513* (2013.01); *C12Q 2563/137* (2013.01); *C12Q 2563/155* (2013.01); *C12Q 2565/601* (2013.01)

(58) Field of Classification Search
None
See application file for complete search history.

(56) References Cited

U.S. PATENT DOCUMENTS
2016/0137687 A1    5/2016 Sim et al.

OTHER PUBLICATIONS

Khavinson et al., "Short Cell-Penetrating Peptides: A Model of Interactions with Gene Promoter Sites", (2013) Bulletin of Exp. Biol. And Medicine 154(3): 403-408 (Year: 2013).*
Kim (Nan-Micro_small (.First published: Nov. 3, 2016 (2017, vol. 13, 1601926).*
Keren (Science Mag (2002) vol. 297, pp. 72-75).*
Heo ( Langumuir (2015) vol. 31, pp. 13773-13782).*
Lei (Meas. Sci. Technol. 22 (2011) 105802 (7pp).*
Wang (Anal. Chem. 2008, 80, 769-774).*
Pan (J Mol Recognit. 2010 ; 23(2): 232-240. doi:10.1002/jmr.990.).*
Nishinaka T (Journal of American Chemical Society (2005) Conductive metal nanowires templated by the nucleoprotein filaments, complex of DNA and RecA protein. J Am Chem Soc 127, 8120-8125).*
Feng, Jin-An et al., "Hin Recombinase Bound to DNA: The Origin of Specificity in Major and Minor Groove Interactions", *Science*, vol. 263, Jan. 21, 1994 (pp. 348-355).
Schumacher, Maria A. et al., "Crystal Structure of LacI Member, PurR, Bound to DNA: Minor Groove Binding by α Helices", *Science*, vol. 266, Nov. 4, 1994 (pp. 763-770).
Luscombe, Nicholas M. et al., "An overview of the structures of protein-DNA complexes", *Genome biology*, 1.1, 2000 (37 pages in English).
Mukhortava, Ann et al., "Efficient Formation of Site-Specific Protein-DNA Hybrids Using Copper-Free Click Chemistry", *Bioconjugate Chemistry*, 27, 7, Jun. 20, 2016 (pp. 1559-1563).
Kim, Kyung-Il et al., "DNA Binding Peptide Directed Synthesis of Continuous DNA Nanowires for Analysis of Large DNA Molecules by Scanning Electron Microscope", *Small*, vol. 13, Issue 2, Jan. 11, 2017 (pp. 1-7).
International Search Report issued on Feb. 5, 2018 in counterpart International Patent Application No. PCT/KR2017/012117 (3 pages in English and 3 pages in Korean).

* cited by examiner

*Primary Examiner* — Narayan K Bhat
(74) *Attorney, Agent, or Firm* — NSIP Law

(57) ABSTRACT

The present invention relates to a DNA-peptide complex with a high-density functional group, a DNA-peptide-nanomaterial complex and a method for production of the same, a DNA-metal nanowire, and a method for production of the same. The DNA-peptide complex with a high-density functional group may include a DNA molecule; and a peptide containing an amino acid sequence capable of binding to the DNA molecule, wherein the peptide contains at least one functional group at a terminal thereof, wherein the peptide binds to the DNA molecule via at least one of electrostatic interaction, intercalation, and groove binding.

18 Claims, 7 Drawing Sheets
Specification includes a Sequence Listing.

[FIG. 1]
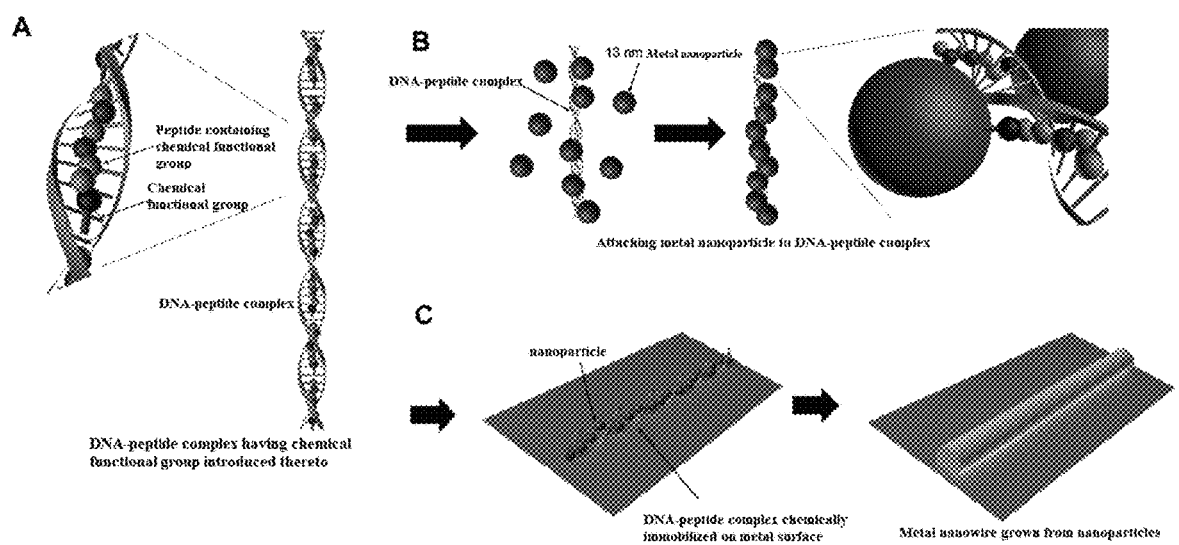

[FIG. 2]
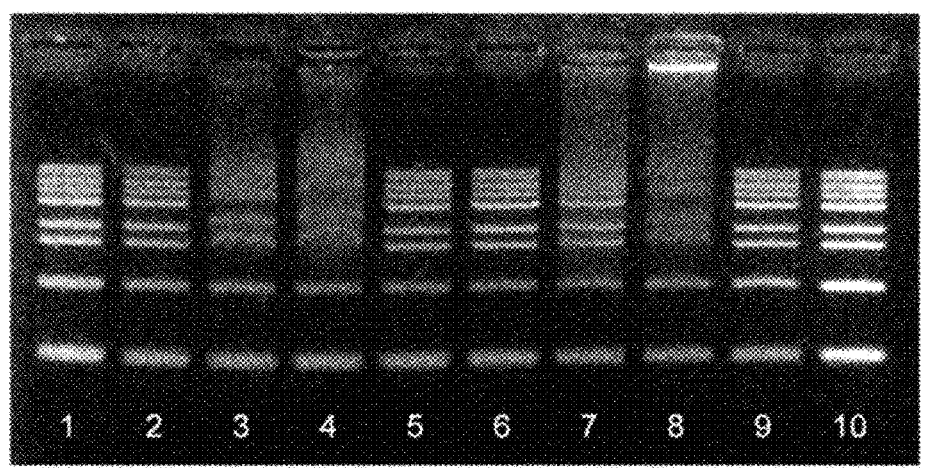

[FIG. 3]
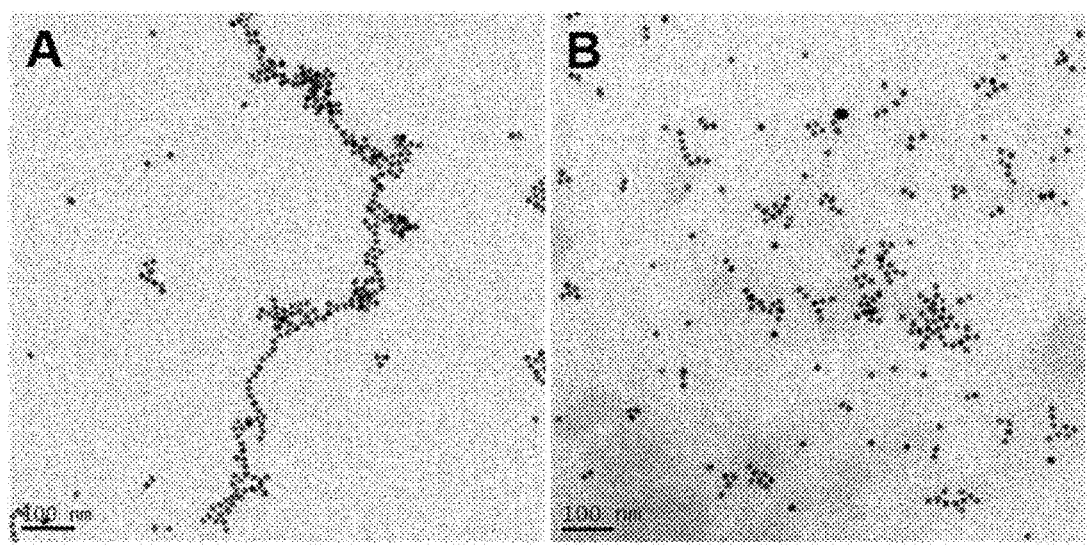

[FIG. 4]
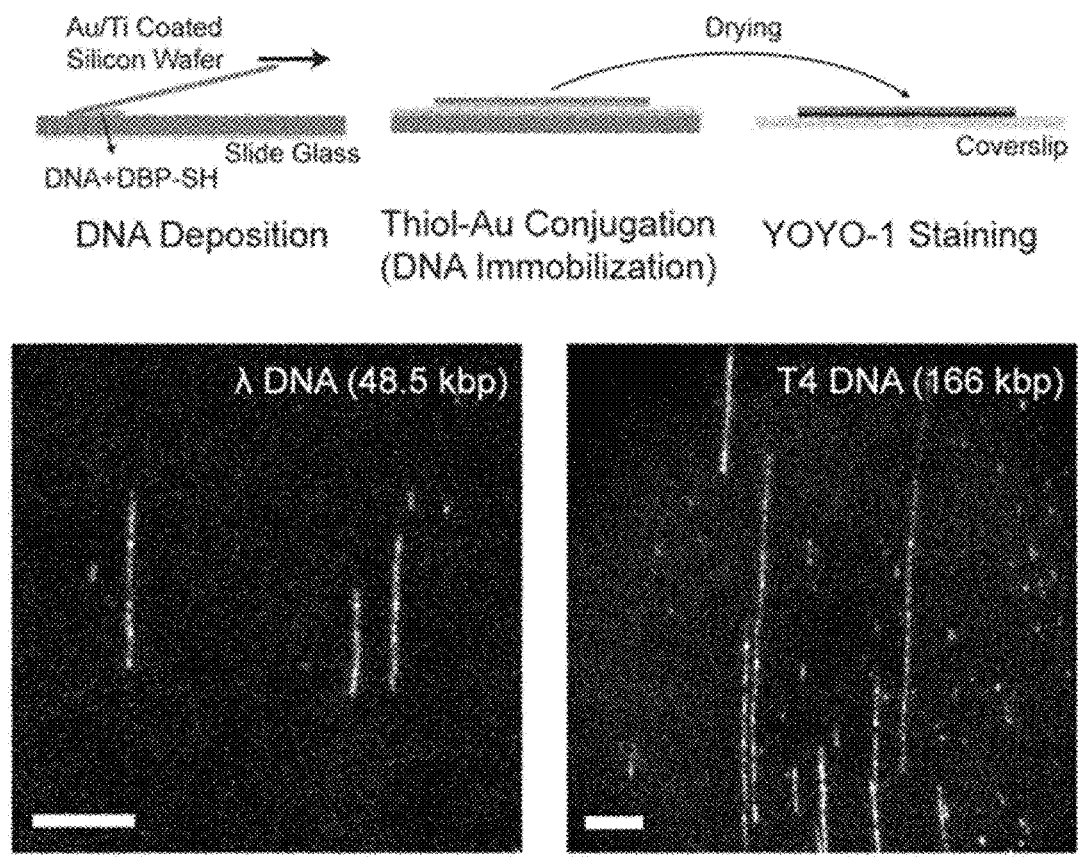

[FIG. 5]
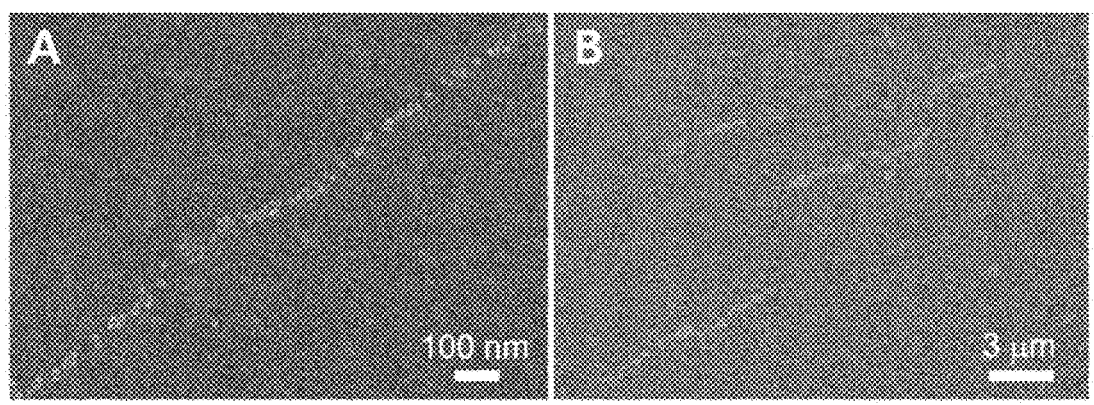

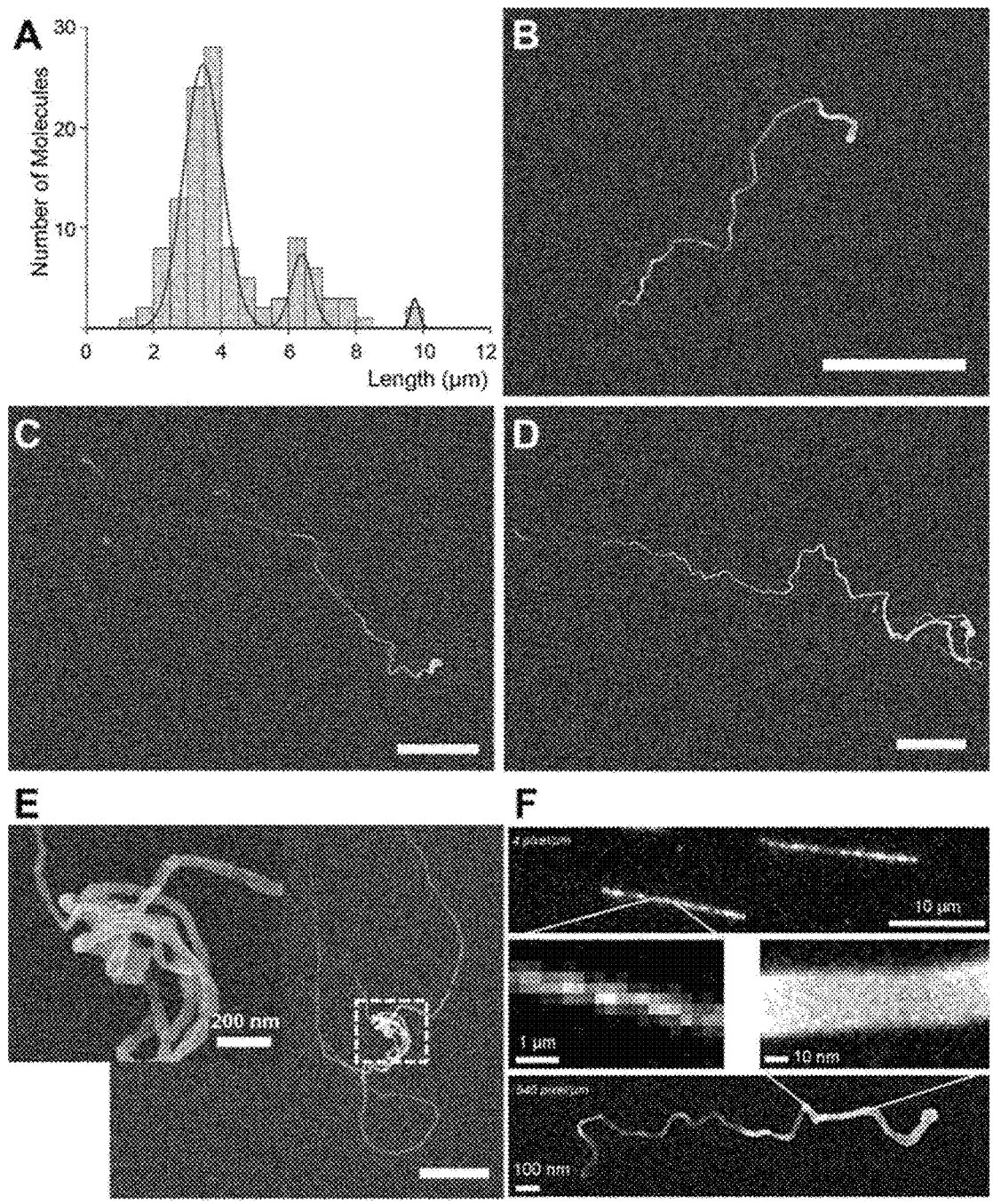
[FIG. 6]

[FIG. 7]
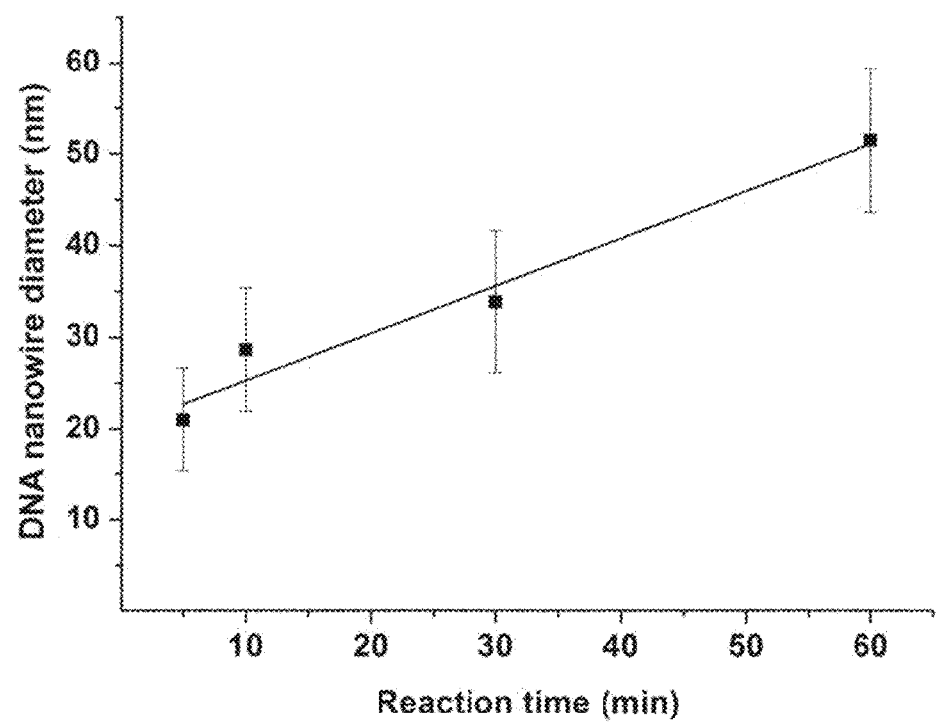

DNA-PEPTIDE COMPOSITE COMPRISING HIGH-DENSITY FUNCTIONAL GROUP, DNA-PEPTIDE-NANOMATERIAL COMPOSITE AND PREPARATION METHOD THEREFOR, AND DNA-METAL NANOWIRE AND MANUFACTURING METHOD THEREFOR

CROSS REFERENCE TO RELATED APPLICATIONS

This application is a U.S. National Stage Application of International Application No. PCT/KR2017/012117, filed on Oct. 31, 2017, which claims the benefit under 35 USC 119(a) and 365(b) of Korean Patent Application No. 10-2016-0142832, filed on Oct. 31, 2016, in the Korean Intellectual Property Office, the entire disclosure of which is incorporated herein by reference for all purposes.

REFERENCE TO SEQUENCE LISTING

The instant application contains a Sequence Listing which has been submitted in ASCII format via EFS-Web and is hereby incorporated by reference in its entirety. Said ASCII Copy, created on Jun. 2, 2022, is named "040950090_Sequence_Listing_ST25.txt" and is 937 bytes in size. The information recorded in the computer readable format is identical to the sequence listing provided in the original specification.

TECHNICAL FIELD

The present disclosure relates to a DNA-peptide-nanomaterial complex containing a DNA-peptide complex with a high-density functional group and a method for production of the same, a DNA-metal nanowire produced from a DNA-peptide-metal particle complex, and a method for production of the same.

RELATED ART

DNA is a nucleic acid with deoxyribose, and forms a body of a gene. Observing DNA molecules is a very important process for obtaining biological information from the DNA molecules. It is very important to visualize DNA molecules for analysis of DNA molecules. The human genome includes 46 chromosomes ($6.4 \times 10^9$ base pairs (bps)) corresponding to 2.2 m of DNA. Chromosome 1, the longest human chromosome, is a single DNA molecule with a length of 85 mm ($2.5 \times 10^8$ bps), while a diameter thereof is only 2 nm. In other words, the chromosome 1 has a width in nanometers and a length in millimeters. Due to this structure of the DNA molecules, it is necessary to be able to visualize DNA with the nanometer scale width and millimeter scale length to comprehensively analyze genomic DNA.

Conventional Methods used for DNA analysis and observation include microscopic methods such as transmission electron microscopy, fluorescence microscopy, and scanning electron microscopy. However, although the transmission electron microscopy has the advantage of observing the detailed structure of DNA, it is difficult to obtain a wide range of high-resolution images using the transmission electron microscopy. The fluorescence microscopy is advantageous in that it is easy to observe molecular scale singularities such as damage in DNA as well as observation of whole molecules of DNA. However, the fluorescence microscopy has a limitation that it is difficult to observe the DNA molecule in a nanometer scale accurately due to the limitation of the resolution using the fluorescence microscopy. The scanning electron microscopy may simultaneously satisfy both the resolution in nanometers and the observation range in millimeters. Thus, the scanning electron microscopy is considered as a method capable of overcoming both disadvantages of the transmission electron microscope and fluorescence microscope. However, the scanning electron microscope also has a limitation that it is difficult to observe the light elements of DNA using the scanning electron microscope.

To overcome these limitations, there is growing interest in methods for metallizing DNA. Although metal nanoparticles functionalized with metal ions or cations are conventionally used to metallize DNA. However, such a method often introduce a specific functional group to the DNA terminal for fixing DNA to the surface of the metal or uses a biomolecule capable of selectively attaching thereto. Thus, there is a disadvantage that only DNA having a specific sequence or shape should be used and a complicated preparation process is required. In addition, the DNA metallization has been performed primarily for the development of electronic devices, not for the DNA analysis. The conventional methods may result in an irregular and unexpected branched form of the DNA after the metallization. Therefore, in the conventional DNA metallization method, the shape of the DNA after the metallization may lose the original shape of the original DNA. Thus, this conventional DNA metallization method the fatal disadvantage as the method for analyzing DNA.

Therefore, it is necessary to research and develop new metallization methods of DNA that can solve these problems and can be used for DNA analysis.

DISCLOSURE

Technical Purpose

One purpose of the present disclosure is to provide DNA-peptide complexes with high-density functional groups.

Another purpose of the present disclosure is to provide DNA-peptide-nanomaterial complexes.

Still another purpose of the present disclosure is to provide a method for production of the DNA-peptide-nanomaterial complex.

Still another purpose of the present disclosure is to provide a method for production of a DNA-metal nanowire from the DNA-peptide-nanomaterial complex.

Still another purpose of the present disclosure is to provide the DNA-metal nanowire.

Technical Solutions

In a first aspect of the present disclosure, there is provided a DNA-peptide complex with a high-density functional group, the complex comprising: a DNA molecule; and a peptide containing an amino acid sequence capable of binding to the DNA molecule, wherein the peptide contains at least one functional group at a terminal thereof, wherein the peptide binds to the DNA molecule via at least one of electrostatic interaction, intercalation, and groove binding.

In one embodiment of the DNA-peptide complex, the function group includes at least one selected from a group consisting of a thiol group (—SH), amine (—NH$_2$), carboxyl (—COOH), cysteine, azide, alkyne, glutaraldehyde, and maleimide.

In one embodiment of the DNA-peptide complex, the peptide contains the functional group at least one of a N-terminal and a C-terminal.

In a second aspect of the present disclosure, there is provided a DNA-peptide-nanomaterial complex, wherein the DNA-peptide-nanomaterial complex contains: the DNA-peptide complex defined above; and a nanomaterial bound to the function group of the peptide at the terminal thereof of the DNA-peptide complex.

In one embodiment of the DNA-peptide-nanomaterial complex, the nanomaterial includes at least one selected from a group consisting of a metal nanoparticle, an oxide nanoparticle, a sulfide nanoparticle, a nanocluster, a quantum dot, a graphene quantum dot, a perovskite, a carbon dot, a polymer particle, a hydroxyapatite, and a magnetic nanoparticle.

In one embodiment of the DNA-peptide-nanomaterial complex, the metal nanoparticle includes at least one selected from a group consisting of gold (Au), silver (Ag), titanium (Ti), copper (Cu), platinum (Pt), palladium (Pd), iron (Fe), zinc (Zn), lead (Pb), tin (Sn), cobalt (Co), nickel (Ni), manganese (Mn), cesium (Cs), indium (In), bismuth (Bi), cadmium (Cd), gallium (Ga), iridium (Ir), aluminum (Al), tantalum (Ta), tungsten (W), vanadium (V), lanthanum (La), manganese (Mn), neodymium (Nd), strontium (Sr), zirconium (Zr), gadolinium (Gd), molybdenum (Mo), ruthenium (Ru), and rhenium (Re).

In a third aspect of the present disclosure, there is provided a method for producing a DNA-peptide-nanomaterial complex, the method comprising: binding a DNA molecule and a peptide each other to form a DNA-peptide complex having a high-density functional group, wherein the peptide contains an amino acid sequence capable of binding to the DNA molecule and at least one functional group at a terminal thereof; and contacting the DNA-peptide complex with a nanomaterial to chemically bind the DNA-peptide complex to the nanomaterial.

In one embodiment of the method of the third aspect, the method further comprises, after forming the DNA-peptide complex with the high-density functional group, contacting the DNA-peptide complex with the high-density functional group to a substrate to immobilizing the complex on the substrate.

In one embodiment of the method of the third aspect, the substrate includes at least one of metal, glass, and silicon substrates.

In one embodiment of the method of the third aspect, the method further comprises, after chemically binding the DNA-peptide complex to the nanomaterial, washing the DNA-peptide complex in contact with the nanomaterial to remove unbound nanomaterials and physically bound nanomaterials.

In one embodiment of the method of the third aspect, the nanomaterial includes at least one selected from a group consisting of a metal nanoparticle, an oxide nanoparticle, a sulfide nanoparticle, a nanocluster, a quantum dot, a graphene quantum dot, a perovskite, a carbon dot, a polymer particle, a hydroxyapatite, and a magnetic nanoparticle.

In one embodiment of the method of the third aspect, the metal nanoparticle includes at least one selected from a group consisting of gold (Au), silver (Ag), titanium (Ti), copper (Cu), platinum (Pt), palladium (Pd), iron (Fe), zinc (Zn), lead (Pb), tin (Sn), cobalt (Co), nickel (Ni), manganese (Mn), cesium (Cs), indium (In), bismuth (Bi), cadmium (Cd), gallium (Ga), iridium (Ir), aluminum (Al), tantalum (Ta), tungsten (W), vanadium (V), lanthanum (La), manganese (Mn), neodymium (Nd), strontium (Sr), zirconium (Zr), gadolinium (Gd), molybdenum (Mo), ruthenium (Ru), and rhenium (Re).

In one embodiment of the method of the third aspect, the function group includes at least one selected from a group consisting of a thiol group (—SH), amine (—$NH_2$), carboxyl (—COOH), cysteine, azide, alkyne, glutaraldehyde, and maleimide.

In a fourth aspect of the present disclosure, there is provided a method for producing a DNA-metal nanowire, the method comprising: binding a DNA molecule and a peptide each other to form a DNA-peptide complex having a high-density functional group, wherein the peptide contains an amino acid sequence capable of binding to the DNA molecule and at least one functional group at a terminal thereof; chemically binding the DNA-peptide complex to a metal nanoparticle to produce a DNA-peptide-metal nanoparticle complex; immersing the DNA-peptide-metal nanoparticle complex in a metal growth solution containing a reducing agent; and removing the metal growth solution.

In one embodiment of the method of the fourth aspect, the method further comprises, after removing the metal growth solution, a washing step to remove unbound metal nanoparticles and physically bound metal nanoparticles.

In one embodiment of the method of the fourth aspect, the metal nanoparticle includes at least one selected from a group consisting of gold (Au), silver (Ag), titanium (Ti), copper (Cu), platinum (Pt), palladium (Pd), iron (Fe), zinc (Zn), lead (Pb), tin (Sn), cobalt (Co), nickel (Ni), manganese (Mn), cesium (Cs), indium (In), bismuth (Bi), cadmium (Cd), gallium (Ga), iridium (Ir), aluminum (Al), tantalum (Ta), tungsten (W), vanadium (V), lanthanum (La), manganese (Mn), neodymium (Nd), strontium (Sr), zirconium (Zr), gadolinium (Gd), molybdenum (Mo), ruthenium (Ru), and rhenium (Re).

In one embodiment of the method of the fourth aspect, the function group includes at least one selected from a group consisting of a thiol group (—SH), amine (—$NH_2$), carboxyl (—COOH), cysteine, azide, alkyne, glutaraldehyde, and maleimide.

In a fifth aspect of the present disclosure, there is provided a DNA-metal nanowire produced by the method for production of the DNA-metal nanowire, wherein the DNA-metal nanowire includes a DNA molecule; a peptide containing an amino acid sequence capable of binding to the DNA molecule, wherein the peptide contains at least one functional group at a terminal thereof; and a metal nanoparticle, wherein the peptide binds to the DNA molecule via at least one of electrostatic interaction, intercalation, and groove binding, wherein the DNA-metal nanowire includes a DNA-peptide-metal nanoparticle complex containing the metal nanoparticle bound to the function group of the peptide terminal, and a metal coating coupled to the DNA-peptide-metal nanoparticle, and covering the DNA-peptide-metal nanoparticle.

Technical Effects

According to the present disclosure, a functional group can be easily introduced onto a DNA molecule by using the DNA-binding peptide, onto which otherwise conventionally the functional group may not be introduced. Further, the DNA-peptide complex with a high-density functional group can be provided. Furthermore, a DNA-peptide-nanomaterial complex can be easily formed via a combination between a functional group and a nanomaterial. DNA is chemically bonded to the nanomaterial via the peptide and functional groups of the peptide, allowing physically bound materials to be easily removed by washing. In addition, the present disclosure does not directly introduce nanomaterial onto DNA. Rather, in accordance with present disclosure, the DNA is bound to the nanomaterial via the peptide function group to form the DNA complex. Thus, DNA may form complexes with nanomaterials to which DNA is conventionally not bound, to form the DNA complex. Accordingly, various kinds of DNA and nanomaterials can be used. When metal nanoparticles are used as nanomaterials, DNA can be metallized by forming the DNA-peptide-metal nanoparticle complex. Further, when using the metal nanoparticles bound to DNA molecules as a medium, the present disclosure may form smooth metal nanowires having the uniform width and length based on the DNA structure. In this connection, the thickness of the nanowires can be controlled by adjusting the metallization time. The easy metallization of DNA according to the present disclosure may allow imaging DNA more clearly and at a high resolution using the scanning electron microscope (SEM). This allows analyzing various structures of DNAs, such as DNA dimer, trimer, and DNA three-dimensional structure, as well as the single-molecule DNA in a more accurate and in a detailed manner.

BRIEF DESCRIPTION OF THE DRAWINGS

FIG. 1 shows a DNA-peptide complex and a DNA-peptide-metal-nanoparticle complex in accordance with the present disclosure.

FIG. 2 is a diagram for illustrating complexes according to embodiments of the present disclosure.

FIG. 3 is an illustration of a DNA-peptide-nanomaterial complex according to one embodiment of the present disclosure.

FIG. 4 illustrates immobilization to a substrate of a DNA-peptide complex with a high-density functional group according to one embodiment of the present disclosure.

FIG. 5 is an illustration of DNA-peptide-nanomaterial complexes according to embodiments of the present disclosure.

FIG. 6 is an illustration of a DNA-metal nanowire according to another embodiment of the present disclosure.

FIG. 7 is an illustration of a DNA-metal nanowire according to still another embodiment of the present disclosure.

DETAILED DESCRIPTIONS

Hereinafter, embodiments of the present disclosure will be described in detail with reference to the accompanying drawings. Embodiments of the present disclosure is to be considered as illustrative and not restrictive since the present disclosure may include numerous modifications and various form. The particular embodiments are illustrated by way of example in the drawings and will be described in detail. It should be understood, however, that the present disclosure is not intended to be limited to any particular form, but includes all modifications, equivalents, and alternatives falling within the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A DNA-peptide complex with a high-density functional group according to the present disclosure includes a DNA molecule; and a peptide containing an amino acid sequence capable of binding to the DNA molecule, wherein the peptide contains at least one functional group at a terminal thereof, wherein the peptide binds to the DNA molecule via at least one of electrostatic interaction, intercalation, and groove binding.

DNA (deoxyribonucleic acid) molecule is a nucleic acid with deoxyribose, and forms a body of a gene. As used herein, a DNA molecule may use any DNA, regardless of a structure and length thereof. In one example, DNA may be λDNA. λDNA is a double stranded DNA having a length of 48,502 bp and is a representative natural DNA having a nano-scale width and a micron-scale length.

A peptide is a compound in which two or more α-amino acids are linked via a peptide bond. The peptide in accordance with the present disclosure may be a peptide capable of binding to DNA. In this connection, the peptide contain an amino acid sequence interacts with DNA to capable of binding to DNA. In one example, the amino acid sequence that can bind to the DNA may include at least one of lysine (Lys), tryptophan (Trp), arginine (Arg), histidine (His), phenylalanine (Phe) and tyrosine (Tyr).

The peptide binds to the DNA molecule via at least one of the electrostatic interaction, intercalation, and groove binding.

The peptide according to the present disclosure contains positively charged amino acid residues and can electrostatically interact with normally negatively charged DNA molecules. In this connection, the peptide that binds to the DNA via electrostatic interaction may contain an amino acid sequence that includes at least one of arginine, histidine, and lysine. Further, the peptide according to the present disclosure may bind to the DNA via groove binding or via intercalation, in addition to the electrostatically interaction. Alternatively, the peptide according to the present disclosure may bind to the DNA via groove binding and intercalation, in addition to the electrostatically interaction. The groove binding refers to binding between an exposed base of the DNA and the peptide. In this connection, the peptide can bind to the DNA via groove binding. Intercalation refers to a phenomenon in which molecules, atoms and ions are inserted between layers of a layered material. In this connection, the peptide can be inserted into double strands of DNA. In this connection, the peptide that is intercalated with the DNA may contain an amino acid sequence including the amino acid with an aromatic ring such as at least one of phenylalanine, tyrosine, and tryptophan.

The peptide according to the present disclosure, as illustrated above, contains at least one amino acid capable of binding to DNA, and, thus, can bind to DNA molecule via at least one of electrostatic interaction, intercalation, and groove binding. Although the exemplary peptides capable of binding to DNA are exemplified, the present disclosure is not limited thereto.

Further, the peptide according to the present disclosure may contain one or more function groups at both terminals of the peptide, that is, at least one of the N-terminal and C-terminal thereof. In this connection, the function group may be combined with a nanomaterial. In one example, the functional group may include thiol group (—SH), amine (—NH$_2$), carboxyl (—COOH), cysteine, azide, alkyne, glutaraldehyde, and maleimide. The peptide can bind to the DNA to introduce the functional group to the DNA molecule. Controlling the density and type of the function group introduced to the peptide terminal may control the function group in the DNA-peptide complex. In this connection, a large number of peptides, each having at least one function group is bound to the DNA molecule, such that a DNA molecule bonded with the peptide contain a high-density functional group.

The DNA-peptide complex may be attached to a substrate. The substrate may be embodied as a metal, glass, silicon, etc. The substrate may have various composition, shape, and size. In one example, when the substrate is a metal substrate, the metal substrate may be a thin film itself formed of a metal or a substrate containing a metal thin-film as the surface thereof. That is, the metal substrate according to the present disclosure may not only be a metal substrate itself, but may also be a substrate containing a metal thin-film formed thereon via coating or lamination of metal. The DNA-peptide complex can be bound to and thus immobilized on the substrate surface via the function group of the DNA-peptide complex. That is, the DNA-peptide complex immobilized on the substrate may have a DNA-peptide-substrate structure.

The DNA-peptide-nanomaterial complex according to the present disclosure contains a DNA-peptide complex with a high-density functional group according to the present disclosure exemplified above, and a nanomaterial combined with a functional group introduced onto the peptide terminal of the DNA-peptide complex.

The nanomaterial can bind to the peptide terminal function group and thus bind to the DNA molecule via the peptide terminal function group. That is, the DNA-peptide-nanomaterial complex according to the present disclosure can exhibit a structure in which the DNA-peptide complex is combined with the nanomaterial via the function group at the terminal of the peptide bound to a DNA molecule. In this connection, the peptide may bind to the nanomaterial and the DNA molecule, respectively, thereby to act as a linker between the nanomaterial and the DNA molecule.

The nanomaterial may include at least one of a metal nanoparticle, an oxide nanoparticle, a sulfide nanoparticle, a nanocluster, a quantum dot, a graphene quantum dot, a perovskite, a carbon dot, a polymer particle, a hydroxyapatite, and a magnetic nanoparticle. In one example, the metal nanoparticle may be made of at least one selected from a group consisting of gold (Au), silver (Ag), titanium (Ti), copper (Cu), platinum (Pt), palladium (Pd), iron (Fe), zinc (Zn), lead (Pb), tin (Sn), cobalt (Co), nickel (Ni), manganese (Mn), cesium (Cs), indium (In), bismuth (Bi), cadmium (Cd), gallium (Ga), iridium (Ir), aluminum (Al), tantalum (Ta), tungsten (W), vanadium (V), lanthanum (La), manganese (Mn), neodymium (Nd), strontium (Sr), zirconium (Zr), gadolinium (Gd), molybdenum (Mo), ruthenium (Ru), and rhenium (Re). Those elements may be contained in a single manner or in combination thereof. That is, the metal nanoparticle according to the present disclosure may be made of each of the metals alone or of alloys thereof.

The DNA-peptide-nanomaterial complex according to the present disclosure may be immobilized on the substrate, as described above with reference to the DNA-peptide complex. In this connection, a function group that does not bind to the nanomaterial among the peptide function groups in the complex may be bound to the substrate such that the DNA-peptide-nanomaterial complex may be immobilized on the substrate.

Hereinafter, more specifically, referring to FIG. 1, the DNA-peptide-metal nanoparticle complex according to the present disclosure will be exemplified using specific embodiments in which a DNA molecule employs a double-stranded DNA (dsDNA), and the nanomaterial employs metal nanoparticles or metal thin-film.

FIG. 1 illustrates a DNA-peptide complex and a DNA-peptide-metal nanoparticle complex according to the present disclosure.

In FIG. 1, A is a plot of a DNA-peptide complex having a high-density functional group in which a peptide containing a function group is coupled with a DNA molecule. B is a diagram for illustrating a case where the nanomaterial is a metal nanoparticle. C is a diagram illustrating a case where a DNA-peptide-metal particle complex having a high-density functional group is attached to a metal thin-film substrate.

As shown in FIG. 1, the DNA-peptide complex may form the DNA-peptide complex with a high-density functional group in which the DNA molecule is coupled with a peptide having a functional group tagged on a terminal thereof. In other words, a structure may be obtained in which many peptides are inserted in the DNA molecule (A in FIG. 1). In this connection, when the nanomaterial is a metal nanoparticle, a DNA molecule coupled to the peptide, that is, a DNA-peptide complex may result in a DNA-peptide-metal nanoparticle complex structure via a bond between the functional group tagged on the peptide terminal and the metal nanoparticle (B in FIG. 1).

Further, a DNA molecule associated with the peptide, that is, a DNA-peptide complex, can be immobilized on a metal thin-film via a bond between the functional group of the peptide and the metal thin-film surface (not shown). In this connection, some of the functional groups of the peptides bind to the metal thin-film, thereby to fix the DNA-peptide complex on the metal thin-film surface, while the rest of the function groups may be combined with the metal nanoparticles (C in FIG. 1). In this connection, the metal nanoparticles of the DNA-peptide-metal nanoparticle complex according to the present disclosure may act as seed particles. When the metal is grown using the metal nanoparticle as the seed, the DNA-peptide-metal nanoparticle complex according to the present disclosure may result in a metal nanowire structure (DNA-based metal nanowire) that represents the structure of DNA (C in FIG. 1). More specific examples thereof will be described later.

A method for producing a DNA-peptide-nanomaterial complex according to the present disclosure comprises combining a DNA molecule with a peptide, the peptide containing an amino acid sequence capable of binding to the DNA molecule and at least one functional group at the terminal thereof, thereby forming a DNA-peptide complex having a high-density functional group; and contacting the DNA-peptide complex with a nanomaterial, thereby chemically bonding the DNA-peptide complex to the nanomaterial.

The DNA molecule, peptide, DNA-peptide complex with various function groups, and nanomaterial are substantially the same as those exemplified above. Details thereof as are duplicated herein will be omitted and differences therebetween will be mainly described later.

In one example, the binding reaction between the DNA molecule and the peptide may be performed by mixing solutions containing the DNA molecule and the peptide respectively with each other. In this connection, the DNA molecule contacts the peptide. Thus, as illustrated above, the DNA-peptide complex may be formed via at least one of the electrostatic interactions, intercalation, and groove binding between the DNA molecule and the peptide.

The DNA molecule may be bound to multiple peptides. Due to the multiple function groups introduced onto the peptides, the DNA-peptide complex may contain multiple functional groups. Because of the complexity of introducing function groups, the functional groups may not be conventionally and easily introduced onto DNA molecules. However, in accordance with the present disclosure, the functional groups may be easily introduced onto DNA molecules using the peptides. Accordingly, DNA-peptide complex according to the present disclosure may contain high-density functional groups.

In this connection, after forming the DNA-peptide complex with the high-density functional group, the method may further comprise contacting the DNA-peptide complex having the high-density functional group with the substrate to immobilize the complex on the substrate. In this connection, the substrate is substantially the same as described above. Thus, details thereof as are duplicated herein will be omitted, and differences will be mainly described later. In one example, when the substrate is a metal thin-film, the method may react the DNA-peptide complex with the metal thin-film to form a DNA-peptide-metal thin-film complex immobilized on the metal thin-film surface. In this connection, the reaction between the DNA-peptide complex and the metal thin-film may be performed by contacting the metal thin-film with a solution containing the DNA-peptide complex.

The DNA-peptide complex reacts with the nanomaterial such that the chemical bonding of the function group of the DNA-peptide complex and the surface of the nanomaterial may occur. Thus, the DNA-peptide-nanomaterial complex may be obtained in which the DNA molecule and the nanomaterial are coupled to each other via the peptide.

In this connection, when the DNA-peptide complex is reacted with the metal nanoparticle, this may form a DNA-peptide-metal nanoparticle complex. In this connection, the reaction between the DNA-peptide complex and the metal nanoparticle may be performed by mixing solutions containing the DNA-peptide complex and the metal nanoparticles respectively with each other.

In one example, when the DNA-peptide complex is reacted with both the metal nanoparticles and metal thin-film (substrate), some of the function groups of the DNA-peptide complex bind to the metal thin-film, such that the DNA-peptide complex is fixed to the metal thin-film (thus, forming the DNA-peptide-metal thin-film complex), while the rest of the function groups of the DNA-peptide complex, which are not coupled with the metal thin-film, may bind to the metal nanoparticles to form the DNA-peptide-metal nanoparticle complex. As a result, the DNA-peptide-metal complex may be obtained in which the DNA-peptide complex is bound to both of the metal particles and metal thin-film. In this connection, preferably, the DNA-peptide complex is first reacted with the metal thin-film to fix the DNA-peptide complex to the metal thin-film, and, then, the DNA-peptide complex is reacted with the metal particles.

Further, the method, may include, after immobilizing the DNA-peptide complex on the substrate and then chemically combining the DNA-peptide complex immobilized on the substrate with the nanomaterial, washing the DNA-peptide complex in contact with the substrate and the nanomaterial to remove unbound nanomaterials and physically bound nanomaterials. In this connection, the DNA-peptide complex in combination with the substrate and nanomaterial is chemically bound to the substrate and the nanomaterial via the function group of the complex. Thus, Thus, the washing may easily remove unreacted and non-specifically bound materials such as unbound nanomaterial, physically bound nanomaterial, or foreign substance from the DNA-peptide complex immobilized to the substrate.

According to the production method of the DNA-peptide-nanomaterial complex according to the present disclosure, using the peptide as a linker makes it possible to easily combine DNA of various lengths and structures with various substrates and nanomaterials without difficulty in introducing the function groups. Further, when a metal substrate is used as a nanomaterial, various DNA can be easily metallized. Further, the metallized DNA, that is, the DNA-peptide-metal particle complex may maintain the shape of DNA.

In one example, when the nanomaterial includes a metal nanoparticle, the DNA-peptide-metal nanoparticle complex may be further metallized. In this connection, the further metallized DNA-peptide-metal nanoparticle complex may be in a form of a DNA-based metal nanowire. More details thereof will be specifically described below.

A method for producing a DNA-metal nanowire according to the present disclosure may include combining a DNA molecule with a peptide, the peptide having an amino acid sequence capable of binding to the DNA molecule and containing at least one functional group at the terminal thereof, thereby to form a DNA-peptide complex with a high-density functional group; and chemically bonding the DNA-peptide complex with a metal nanoparticle.

In this connection, the DNA-peptide complex may be a DNA-peptide complex immobilized on a substrate.

Subsequently, the method may include immersing the DNA-peptide-metal nanoparticle complex in a metal growth solution containing a reducing agent and removing the metal growth solution.

The DNA molecule, the peptide, the DNA-peptide complex having the high-density functional group, the metal nanoparticle, and the DNA-peptide-metal-nanoparticle complex are substantially the same as described above. The overlapping detailed description therebetween will be omitted and differences will be described below.

The DNA-peptide complex coupled with the metal nanoparticle (DNA-peptide-metal nanoparticle complex) may be further metallized by growing the metal using the metal particle of the complex as a seed. The further-metallized DNA-peptide-metal nanoparticle complex may have the same shape as that of the metal nanowire. In other words, according to the present disclosure, the further metallization of the DNA-peptide-metal particle complex may result in formation of a DNA-based, smooth metal-nanowire (DNA-metal nanowire) that maintains the original structures of DNAs of various lengths and structures.

In this connection, the metallization degree of the DNA-metal nanowire may be controlled by adjusting the reaction time between the DNA-peptide-metal nanoparticle complex and the metal growth solution, that is, the time duration for which the DNA-peptide-metal nanoparticle complex is immersed in the metal growth solution. As a result, a width thickness of the DNA-metal nanowire can be controlled. In one example, the reducing agent may be ascorbic acid.

Further the method may include, after removing the metal growth solution, a washing step for removing non-bound substances and the physically bound substances.

The DNA-metal nanowire according to the present disclosure may include the DNA-peptide-metal nanoparticle complex and a metal coating coupled to the DNA-peptide-metal nanoparticle complex, and covering the DNA-peptide-metal nanoparticle complex.

As described above, in the DNA-metal nanowire, a metal grows using a metal particle of the DNA-peptide-metal nanoparticle complex as a seed, and thus the DNA-metal nanowire may maintain the original structure of the DNA, and may have a smooth and uniform shape and width.

As described above, the metallized DNA, that is, the DNA-peptide-metal nanoparticle complex and the DNA-metal nanowire according to the present disclosure may have the original structure of DNA and may be used to comprehensively analyze the DNA. In one example, the metalized DNA according to the present disclosure may be observed and analyzed at a high resolution and in a more detailed manner via a scanning electron microscope (SEM) than when using the conventional DNA analysis method. Thus, the metalized DNA according to the present disclosure may be applied to the analysis of the base sequence of DNA, DNA-protein complex formation, and the like. In addition, according to the present disclosure, it is possible to metallize DNA of the same kind and of various lengths, that is, dimers, trimers, etc. of DNA. Thus, the metallized DNA may be used to check structures of DNA and to check the three-dimensional entangle form of DNA having polymer properties.

Hereinafter, the present disclosure will describe in more detail the DNA-peptide, DNA-peptide-nanomaterial complex and a production method thereof, DNA-metal nanowire and a production method thereof according to the present disclosure.

First, in order to produce a DNA-peptide complex, a C-terminus thiol-tagged DNA binding peptide having the sequence KWKWKKA (SEQ ID NO: 1) (DBP-SH, KWKWKKA-SH) with amino acid sequences including lysine and tryptophan was mixed to ΔDNA in each of molar ratios 1:100, 1:500, and 1:1000. The mixtures were incubated for 1 hour at room temperature to produce DNA-(DBP-SH) complexes 1 to 3. The C-terminal thiol-tagged DNA-binding peptides were purchased from Peptron (Daejeon, Korea). A computer readable format of SEQ ID NO: 1 is submitted and incorporated herein. The information recorded in the computer readable format is identical to the Sequence Listing provided in this specification.

Next, a solution containing 13 nm gold nanoparticles (AuNP) was added to each of solutions containing the DNA-(DBP-SH) complexes 1 to 3 respectively, which, in turn, was incubated for 1 hour to produce DNA-(DBP-SH)-AuNP complexes 1 to 3. In this connection, the concentrations of DBP-SH and gold nanoparticles were the same in each sample.

The 13 nm gold nanoparticle containing solution was prepared by adding 2 mL of $HAuCl_4$ solution (50 mM) to 98 mL of deionized water, and by adding trisodium citrate dihydrate solution (38.8 mM, 10 mL) thereto under reflux and by cooling the mixed solution to a room temperature while continuous stirring thereof. Further, in order that the reactivity between the thiolate moieties and the gold nanoparticles is preserved, but in order to minimize aggregation between the gold nanoparticles, the gold nanoparticles were passivated with polyvinylpyrrolidone (PVP). In this connection, the polyvinylpyrrolidone (PVP) (10 μM, MW: 10,000) was added to the gold nanoparticle solution containing at the same volume content as that of the gold nanoparticle suspension, and then the mixture was incubated overnight. Thereafter, the gold nanoparticle-PVP (AuNP-PVP) solution was centrifuged at 16,700 rpm for 15 minutes, and thus a supernatant was subjected to decantation. This decantation was repeated three times to remove free PVP molecules. $HAuCl_4$, trisodium citrate, and polyvinylpyrrolidone (PVP, MW: 10,000) were purchased from Sigma-Aldrich (USA).

The samples were thoroughly washed with sodium dodecyl sulfate (SDS) surfactant solution and deionized water after each step to minimize non-specific binding of the gold nanoparticles to surfaces of the samples.

In a comparative example, C-terminal thiol-tagged non-binding peptides having the sequence EWEWEEA (SEQ ID NO: 2) (NBPSH, EWEWEEA-SH) were mixed to ΔDNA at a molar ratio of 1:1000. The mixture was incubated for 1 hour at a room temperature. The C-terminal thiol-tagged non-binding peptide was purchased from Peptron (Daejeon, Korea). A computer readable format of SEQ ID NO: 2 is submitted and incorporated herein. The information recorded in the computer readable format is identical to the Sequence Listing provided in this specification.

Further, a solution containing 13 nm gold nanoparticles was added to the NBP-SH treated DNA, followed by incubation for 1 hour. In this connection, the concentrations of NBP-SH and gold nanoparticles are the same.

Next, DNA-(DBP-SH) complexes 1 to 3 and DNA-(DBP-SH)-AuNP complexes 1 to 3 according to Present Examples, and NBP-SH treated DNA and DNA treated with NBP-SH and gold nanoparticles in accordance with the Comparative Example were subject to gel-electrophoresis. In this connection, as control, a 1 kb DNA ladder was diluted with deionized water at a concentration of 250 ng/μl. Each sample was loaded with 1.3% agarose gel and then electrophoresed at 130 V for 30 minutes. The gel was then stained with SYBR Gold for 30 minutes. Results are shown in FIG. 2.

FIG. 2 is a diagram for illustrating complexes according to Present Examples according to the present disclosure.

In FIG. 2, each of lanes 1 and 10 represents, as the control, 1 kb DNA ladder. Lanes 2 to 4 respectively represent DNA complexes 1 to 3 treated with DBP-SH at molar ratios of 1:100, 1:500, and 1:1000, that is, the DNA-(DBP-SH) complexes 1 to 3. A lane 5 represents DNA treated with NBP-SH at a ratio of 1:1000. Lanes 6 to 8 respectively represent DNA-(DBP-SH) complexes 1 to 3 treated with 13 nm AuNP, that is, DNA-(DBP-SH)-AuNP complexes 1 to 3. A lane 9 represents DNA treated with NBP-SH and then treated with 13 nm AuNP.

Referring to FIG. 2, a comparison between the lanes 2 to 4 reveals that the DNA-(DBP-SH) complex treated with a higher DBP-SH concentrations in the electrophoretic gel exhibits a wider and smearing band pattern. This means that DNA interacts with the DBP-SH, that is, the peptide is introduced onto DNA. Further, it may be seen that the interaction between DNA and DBP-SH increases with increasing concentration of the DBP-SH.

When comparing the lane 5, DNA-treated with NBP-SH as the Comparative Example with DNA-(DBP-SH) complexes (lanes 2 to 4), it may be seen that DNA treated with NBP-SH does not show band widening and smearing. This may mean that the DBP-SH, as a peptide having a thiol group and having an amino acid sequence including lysine and tryptophan, shows affinity with the double-stranded DNA molecules and can bind to the DNA molecules, whereas, the NBP-SH, as a peptide that contains the same thiol group but having glutamate (E) residues as negatively charged replacing lysine (K) residues as positively charged, does not bind to DNA. That is, it may be confirmed that a peptide having an amino acid sequence including lysine and tryptophan binds to double-stranded DNA molecules. This indicates that the peptide having an amino acid sequence including lysine and tryptophan uniformly binds to double-stranded DNA molecules via tryptophan intercalation and electrostatic interactions involving positively charged lysine residues.

Further, when comparing the DNA-(DBP-SH) complexes treated with gold nanoparticles, that is, DNA-(DBP-SH)-AuNP complexes 1 to 3 (lanes 6 to 8) each other, it may be seen that DNA-(DBP-SH)-AuNP complexes have similar tendency based on the concentration of gold nanoparticles to those of DNA-(DBP-SH)-AuNP complexes based on the concentrations of DBP-SH. In particular, it may be seen that the DNA-(DBP-SH)-AuNP complexes exhibit a bright band near a well. This means that the DNA-(DBP-SH)-AuNP complexes did not migrate freely because the complexes were trapped in the sample introduction portion during gel electrophoresis. That is, this means that the DNA-(DBP-SH) complexes bind to gold nanoparticles.

Further, the DNA (lane 9) treated with NBP-SH and gold nanoparticles did not exhibit band widening and smearing as described in the DNA treated with the NBP-SH (lane 5). This means that both of NBP-SH and AuNP have little interaction with DNA, regardless of the presence of gold nanoparticles.

More specifically, DNA-(DBP-SH)-AuNP complex was photographed with a TEM to check the binding of DNA coupled to the DBP-SH to the gold nanoparticles as a nanomaterial of the DNA-peptide complex. Results are shown in FIG. 3.

FIG. 3 is a diagram for describing the DNA-peptide-nanomaterial complex according to one Present Example according to the present disclosure.

In FIG. 3, A shows a TEM image of gold nanoparticles assembled with the DNA backbone. B shows a TEM image of a control as the image of the DNA-(DBP-SH)-AuNP complex, except that NBP-SH was used instead of DBP-SH.

First, referring to A in FIG. 3, it may be seen that 13 nm gold nanoparticles are connected in a linear structure.

As shown in B in FIG. 3, when the DBP-SH was replaced with NBP-SH, gold nanoparticles were distributed randomly rather than linearly, as shown in A in FIG. 3.

This means that, when the DBP-SH treated DNA and gold nanoparticles are reacted with each other, the gold nanoparticles combine with DNA to form a linear structure, whereas DNA treated with NBP-SH did not bind to gold nanoparticles and thus the gold nanoparticles are distributed randomly. In other words, it may be confirmed that the gold nanoparticles successfully bind to DNA bound to peptide (DBP-SH).

Therefore, in general, the peptide (DBP-SH) containing a thiol group and containing an amino acid sequence including lysine and tryptophan reacts with double-stranded DNA to form a DNA-peptide complex. Further, it may be confirmed that, without directly depositing metal ions into the DNA backbone (phosphate backbone and base sequence), the metal nanoparticles may be immobilized on the DNA backbone via the thiol group of the peptide bound to the DNA. That is, according to the present disclosure, the DNA-peptide-metal nanoparticle complexes may be produced.

Whether the DNA-(DBP-SH) complex 3 as produced above was immobilized on a gold-coded substrate was checked. An Au/Ti thin-film film coated Si wafer was prepared using an E-beam evaporator. The thicknesses of Ti/Au were 5 nm/20 nm respectively. The evaporation rate of the two metals was 5 Δ/s. The droplets of DNA-(DBP-SH) complex 3 were then dropped onto the cleaned slide glass. The Au/Ti thin-film coated Si wafer was placed on the droplets to spread and stretch the DNA molecules with the Au/Ti thin-film coated Si wafer and then was dried at 65 degrees C. for 15 minutes. Thereafter, the Si wafer was carefully removed from the slide glass. Further, T4GT7 DNA mixed with DBP-SH at a molar ratio of 1:4000 was used to perform the same process as the above process. Next, in order to confirm whether the DNA-peptide complex was immobilized on an Au/Ti thin-film coated Si wafer, YOYO-1 solution (1 μM 8% β-mercaptoethanol) was dropped onto the cleaned cover glass, and then the Au/Ti thin-film coated Si wafer was placed thereon and dyed. Then, an inverted microscope (Zeiss Observer Al, AG, Germany) with a 63× Zeiss Plan-Neofluar oil immersion objective lens, a solid state laser (Coherent Sapphire 488, Santa Clara, CA) and a corresponding filter set was used together with an electron multiplying charge coupled device digital camera (Evolve EMCCD, Roper Scientific, Tucson, AZ) to view fluorescence images of the samples. Fluorescent images of the samples were generated by software Image Pro Plus (Media Cybernetics, Rockville, Md.) And adjusted with ImageJ software. Results are shown in FIG. 4.

FIG. 4 is a diagram for describing immobilization to a substrate of a DNA-peptide complex with a high-density functional group according to one Present Example according to the present disclosure.

FIG. 4 shows the immobilization of DBP-SH treated DNA (DNA-(DBP-SH)) onto a gold/titanium coated silicon wafer (Au/Ti coated silicon wafer). FIG. 4 show fluorescence images of λDNA (48.5 kb) and T4 DNA (166 kb) immobilized onto the Au/Ti coated surface. Each of the scale bars was 10 μm.

Referring to FIG. 4, the fluorescence images show that the DNA-(DBP-SH) complex is immobilized on the Au/Ti coated silicon wafer surface. In other words, it was confirmed that the Au/Ti coating layer reacted with the DNA-(DBP-SH) complex to form the DNA-(DBP-SH)-metal substrate complex and thus the DNA-(DBP-SH) complex was immobilized onto the Au/Ti coated silicon wafer substrate. Further, it may be confirmed that the DNA-(DBP-SH) complex was immobilized on the Au/Ti coating layer for both of the λDNA and the T4 DNA. This means that various DNA can be metallized and immobilized according to the present disclosure.

In a control experiment, when the same method was performed in the absence of DBP-SH or in the presence of NBP-SH, the binding of DNA on the Au/Ti coated silicon wafer surface was negligible. This means that the DNA can be immobilized onto the gold-thin film via DBP-SH treatment of DNA.

That is, according to the present disclosure, when introducing peptides onto various kinds of DNA, the DNA-peptide complex may be immobilized and metallized on and by the metal-thin-film using the metal-thiol chemistry via the function group of the peptide.

Next, it was confirmed whether DNA-peptide-metal complexes could be visualized using the SEM. 13 nm gold nanoparticles passivated with PVP were reacted with DNA-(DBP-SH) immobilized on the surface of the Au/Ti coated silicon wafer, and then were washed. Results were photographed using the SEM. The results are shown in FIG. 5.

FIG. 5 is a view for describing DNA-peptide-nanomaterial complexes according to the Present Examples according to the present disclosure.

In FIG. 5, A and B are images showing gold nanoparticles (AuNP) in the DNA-(DBP-SH) bound (immobilized) to the Au/Ti coated silicon wafer.

Referring to FIG. 5, on the Au/Ti coated wafers having the DBP-SH treated DNA, that is, the DNA-(DBP-SH) immobilized thereto, gold nanoparticles represented a linear structure as confirmed with reference to A in FIG. 3 and in FIG. 4. This indicates that the SEM may image (visualize) the DNA-peptide complexes immobilized on the gold nanoparticles and gold/titanium coating layer surface. It may be confirmed that gold nanoparticles exhibit a linear structure from an analysis of the images of the DNA-(DBP-SH)-metal complex identified by SEM, as seen in the TEM-imaged samples.

Further, continuing with FIG. 5, we may see that (1) there are few nonspecific binding of gold nanoparticles (bonds other than DNA-peptide complexes) on the Au/Ti coated wafers other than the linear structure of gold nanoparticles on the Au/Ti coated wafers (this may mean that in the immobilization of DNA-(DBP-SH) complex to the metal thin-film (Au/Ti coating), the interaction between metal nanoparticles and charged surfaces that promote non-specific binding of metal nanoparticles may be prevented by the immobilization of DNA-(DBP-SH) complex to the metal thin-film (Au/Ti coating) via metal-thiol covalent bond derived from the DBP-SH); that (2) the PVP passivation of the gold (or metal) nanoparticles can effectively allow gold nanoparticles to have neutral charges while allowing high colloidal stability; and that (3) the stable binding (immobilization) of the DNA-peptide complex onto the metal surface may allow a multiple wash step to remove unreacted metal nanoparticles from the surface.

Further, DNA-based gold nanowires were produced using the DNA-(DBP-SH) complex immobilized on the gold-coated silicon wafer. The (DBP-SH) complex immobilized on the gold-coated surface was reacted with 4.5 nm gold nanoparticles, to produce DNA-(DBP-SH)-metal (gold-coated and gold nanoparticle) complexes. The 4.5 nm gold nanoparticles were prepared by providing 20 mL of HAuCl$_4$/trisodium citrate (250 µM) solution, and magnetically stirring the solution and then by injecting ice-cold sodium borohydride solution (0.1 M) into the solution, and then by culturing the mixed solution for 2 hours at room temperature. Next, the DNA-(DBP-SH)-metal (gold-coated and gold nanoparticle) complexes were washed three times with SDS solution (0.5% w/w) and deionized water in order to remove the non-specific binding and unreacted gold nanoparticles from the gold coated surface. Then, the DNA-(DBP-SH)-AuNP complex was immersed in 375 µL of a gold growth solution and ascorbic acid (100 mM, 2.5 µL) was added thereto. In this connection, the gold growth solution was produced by magnetic stirring and heating of HAuCl$_4$ (250 µM)/cetyltrimethylammonium bromide (80 mM). After completion of the reaction, the surface was washed with 0.5% SDS (0.5% w/w) solution and deionized water three times, to produce a DNA-peptide-metal nanoparticle complex-based gold nanowire (hereinafter referred to as DNA-gold nanowire). This nanowire was photographed by SEM. SEM results are shown in FIG. 6.

FIG. 6 is a view for describing a DNA-metal nanowire according to another Present Example according to the present disclosure.

FIG. 6 shows SEM images of DNA-gold nanowires gold-grown using, as seeds, AuNP of DNA-(DBP-SH)-metal complex according to the present disclosure. In FIG. 6, A shows the histogram of the length distribution of the observed λ-DNA molecules. In FIG. 6, B shows an image of λDNA, C shows an image of dimer of λDNA, D shows an image of trimer of λDNA, and E shows images of entangled molecules. In FIG. 6, F shows a comparison of fluorescence microscopy and SEM images. Each of the scale bars is 1 µm.

Referring to A to D in FIG. 6, DNA-gold nanowires derived from λDNA molecules bound to the gold-coated surface and the gold nanoparticles via the function group of the coupled peptide have the structure of the corresponding λDNA. The peaks of the DNA length distribution correspond to 3.37 µm and 6.54 µm representing λDNA and the dimers of λDNA, respectively. Further, a λDNA trimer molecule may be observed at a length of 9.62 µm.

Referring to E and F in FIG. 6, E and F in FIG. 6 represent elongated but distinct DNA strands. In particular, it may be seen that the entangled form of DNA, which is difficult to identify in conventional DNA metallization methods and analysis, may be clearly distinguished based on the DNA metallization according to the present disclosure (E in FIG. 6). Further, it may be seen that the resolution of the SEM image of the metallized DNA (the bottom image of F in FIG. 6) according to the present disclosure is much higher than that of the image from the conventional fluorescence microscope (the top image of F in FIG. 6). This indicates that the entangled form of DNA is not easily observable under a fluorescence microscope. In particular, the widths of DNA-gold nanowires are only 20 to 30 nm in SEM images, while in optical microscope images, the width of DNA is greater than 0.5 µm, as shown in F in FIG. 3. This comparison shows that SEM analysis can provide more detailed nanometer-scale information on DNA molecules. This means that images with resolutions that cannot be observed with other imaging technologies such as TEM, AFM, and fluorescence microscopy can be obtained using the SEM in accordance with the present disclosure.

Therefore, a DNA-gold nanowire formed from a DNA-(DBP-SH) complex according to the present disclosure can be formed clearly and uniformly (smoothly) in a similar manner to the linear structure of the original DNA. Thus, the DNA-gold nanowire may be imaged at a high resolution using a scanning electron microscope (SEM).

Further, the thickness of the DNA-metal nanowire was measured based on the treatment time of the DNA-peptide complex in the gold growth solution. The results are shown in FIG. 7.

FIG. 7 is a view for describing a DNA-metal nanowire according to another Present Example according to the present disclosure.

FIG. 7 shows that when the DNA-gold nanowire is grown by treatment of the DNA-peptide-metal complex bound to the gold-coated surface and the gold nanoparticle with the gold-grown solution, the thickness of the DNA-gold nanowire is proportional to the time of treatment with the gold growth solution.

Thus, it may be seen that the thickness of the DNA-metal nanowire can be controlled by controlling the treatment time in the metal growth solution.

Comprehensively, as noted above, when combining large DNA molecules with nanomaterials using thiol-tagged DNA binding peptides to the DNA backbone (phosphate backbone and base sequence), the DNA structure can be imaged by a scanning electron microscope. Specifically, because the peptide can bind to double-stranded DNA via the electrostatic charge of the lysine of the peptide and the intercalation of tryptophan of the peptide, the peptide according to the present disclosure can immobilize DNA on the surface of a thin metal film, and can attach metal nanoparticles to DNA templates at the high density of metal nanoparticles together with a minimal background binding of metal nanoparticles to metal thin-film surfaces. Further, the DNA-metal nanowires can preserve the original structure of DNA, and can be easily visualized under the conventional SEM. Thus, information on long DNA molecules can be provided more precisely and accurately via SEM analysis. Thus, when considering the biochemical importance of DNA and the power of scanning electron microscopy for high resolution imaging of large-scale functions of DNA, various biophysical and biochemical molecule events can be identified at the multi-scale level of DNA according to the present disclosure.

Although the above description has been made with reference to the preferred embodiment according to the present disclosure, it will be understood by those skilled in the art that various changes in form and details may be made thereto without departing from the spirit and scope of the present disclosure as set forth in the following claims.

What is claimed is:

1. A method for producing a DNA-peptide-nanomaterial complex, the method comprising:
   binding a double-stranded DNA molecule with a peptide comprising at least one functional group to form a DNA-peptide complex, wherein the peptide contains an amino acid sequence capable of binding to the DNA molecule and the at least one functional group at a terminal of the peptide, wherein the at least one functional group comprises at least one selected from a group consisting of a thiol group (—SH), azide, alkyne, and a combination thereof, and
   wherein the amino acid sequence comprises lysine (K) and tryptophan (W); and
   contacting the DNA-peptide complex with a nanomaterial to form a covalent bond between the nanomaterial and the at least one functional group of the peptide to obtain a DNA-peptide-nanomaterial complex.

2. The method of claim 1, wherein the method further comprises, after forming the DNA-peptide complex, immobilizing the DNA-peptide complex to a substrate.

3. The method of claim 2, wherein the substrate includes at least one of metal, glass, and silicon substrates.

4. The method of claim 2, wherein the method further comprises, after forming a covalent bond between the nanomaterial and the at least one functional group to bind the DNA-peptide complex to the nanomaterial, washing the DNA-peptide-nanomaterial complex to remove unbound nanomaterials.

5. The method of claim 1, wherein the nanomaterial includes at least one selected from a group consisting of a metal nanoparticle, an oxide nanoparticle, a sulfide nanoparticle, a nanocluster, a quantum dot, a graphene quantum dot, a perovskite, a carbon dot, a polymer particle, a hydroxyapatite, and a magnetic nanoparticle.

6. The method of claim 5, wherein the metal nanoparticle includes at least one selected from a group consisting of gold (Au), silver (Ag), titanium (Ti), copper (Cu), platinum (Pt), palladium (Pd), iron (Fe), zinc (Zn), lead (Pb), tin (Sn), cobalt (Co), nickel (Ni), manganese (Mn), cesium (Cs), indium (In), bismuth (Bi), cadmium (Cd), gallium (Ga), iridium (Ir), aluminum (Al), tantalum (Ta), tungsten (W), vanadium (V), lanthanum (La), manganese (Mn), neodymium (Nd), strontium (Sr), zirconium (Zr), gadolinium (Gd), molybdenum (Mo), ruthenium (Ru), and rhenium (Re).

7. The method of claim 1, wherein the functional group comprises a thiol group (—SH).

8. The method of claim 1, wherein the nanomaterial is a gold nanoparticle or a metal nanoparticle, and the nanomaterial is passivated with polyvinylpyrrolidone (PVP) prior to contacting the DNA-peptide complex with the nanomaterial to chemically bind the DNA-peptide complex to the nanomaterial.

9. The method of claim 1, wherein in the step of binding the DNA molecule and the peptide, the DNA molecule and the peptide are mixed in a molar ratio of 1:100; and the peptide is a thiol-tagged DNA binding peptide.

10. The method of claim 1, wherein the at least one functional group comprises a thiol group (—SH), and the amino acid sequence comprises lysine (K), tryptophan (W), and alanine (A) modified with the thiol group (—SH) and does not include glutamate (E).

11. The method of claim 10, wherein the metal nanoparticle includes at least one selected from a group consisting of gold (Au), silver (Ag), titanium (Ti), copper (Cu), and platinum (Pt).

12. A method for producing a DNA-metal nanowire, the method comprising:
  binding a double-stranded DNA molecule with a peptide comprising at least one functional group to form a DNA-peptide complex having a high-density functional group, wherein the peptide contains an amino acid sequence capable of binding to the DNA molecule and the at least one functional group at a terminal thereof; and the at least one functional group comprises at least one selected from a group consisting of a thiol group (—SH), azide, alkyne, and a combination thereof, and
  wherein the amino acid sequence comprises lysine (K) and tryptophan (W);
  forming a covalent bond between the at least one functional group and a metal nanoparticle to produce a DNA-peptide-metal nanoparticle complex;
  immersing the DNA-peptide-metal nanoparticle complex in a metal growth solution containing a reducing agent; and
  removing the metal growth solution.

13. The method of claim 12, wherein the method further comprises, after removing the metal growth solution, a washing step to remove unbound metal nanoparticles and physically bound metal nanoparticles.

14. The method of claim 12, wherein the metal nanoparticle includes at least one selected from a group consisting of gold (Au), silver (Ag), titanium (Ti), copper (Cu), platinum (Pt), palladium (Pd), iron (Fe), zinc (Zn), lead (Pb), tin (Sn), cobalt (Co), nickel (Ni), manganese (Mn), cesium (Cs), indium (In), bismuth (Bi), cadmium (Cd), gallium (Ga), iridium (Ir), aluminum (Al), tantalum (Ta), tungsten (W), vanadium (V), lanthanum (La), manganese (Mn), neodymium (Nd), strontium (Sr), zirconium (Zr), gadolinium (Gd), molybdenum (Mo), ruthenium (Ru), and rhenium (Re).

15. The method of claim 12, wherein the functional group comprises a thiol group (—SH).

16. A method for producing a DNA-peptide-nanoparticle complex, the method comprising:
  binding a peptide to a double-stranded DNA molecule to obtain a DNA-peptide complex,
  wherein the peptide comprises an amino acid sequence capable of binding to the DNA molecule via at least one of electrostatic interaction, intercalation or groove binding, and the peptide comprises the at least one functional group,
  wherein the at least one functional group comprises at least one selected from a group consisting of a thiol group (—SH), azide, alkyne, and a combination thereof, and
  wherein the amino acid sequence comprises lysine (K) and tryptophan (W) and does not include glutamate (E); and
  forming a covalent bond between a metal nanoparticle and the at least one functional group of the peptide in the DNA-peptide complex to obtain a DNA-peptide-nanoparticle complex in which the peptide acts as a linker by linking the metal nanoparticle to the DNA molecule.

17. The method of claim 16, wherein the at least one functional group comprises a thiol group (—SH).

18. The method of claim 16, wherein the peptide is a C-terminus thiol-tagged DNA-binding peptide, and the amino acid sequence comprises lysine (K), tryptophan (W), and alanine (A) modified with the thiol group (—SH).

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Unknown
<220> FEATURE:
<223> OTHER INFORMATION: DNA binding peptide

<400> SEQUENCE: 1

Lys Trp Lys Trp Lys Lys Ala
1               5

<210> SEQ ID NO 2
<211> LENGTH: 7
<212> TYPE: PRT
<213> ORGANISM: Unknown
<220> FEATURE:
<223> OTHER INFORMATION: non-binding peptide

<400> SEQUENCE: 2

Glu Trp Glu Trp Glu Glu Ala
1               5
```